(12) United States Patent
Limousin

(10) Patent No.: US 7,966,065 B2
(45) Date of Patent: Jun. 21, 2011

(54) TREATMENT OF HEART FAILURE BY CONTROLLED ADJUSTMENT OF THE ATRIOVENTRICULAR AND INTERVENTRICULAR DELAYS IN AN ACTIVE IMPLANTABLE MEDICAL DEVICE

(75) Inventor: Marcel Limousin, Paris (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 12/685,573

(22) Filed: Jan. 11, 2010

(65) Prior Publication Data

US 2010/0179608 A1 Jul. 15, 2010

(30) Foreign Application Priority Data

Jan. 9, 2009 (FR) ...................................... 09 00060

(51) Int. Cl.
*A61N 1/00* (2006.01)
(52) U.S. Cl. .......................................................... 607/8
(58) Field of Classification Search ................ 607/9, 17, 607/18
See application file for complete search history.

(56) References Cited

U.S. PATENT DOCUMENTS

| 5,156,154 A | 10/1992 | Valenta, Jr. et al. |
| 5,995,870 A | 11/1999 | Cazeau et al. |
| 6,963,777 B2 * | 11/2005 | Lincoln et al. ................... 607/18 |
| 7,058,450 B2 * | 6/2006 | Struble et al. .................... 607/18 |
| 7,123,962 B2 * | 10/2006 | Siejko et al. ..................... 607/17 |
| 2003/0208240 A1 | 11/2003 | Pastore et al. |
| 2004/0220636 A1 | 11/2004 | Burnes |
| 2008/0243202 A1 | 10/2008 | Patangay et al. |
| 2009/0209875 A1 | 8/2009 | Giorgis et al. |

FOREIGN PATENT DOCUMENTS

| WO | WO 95/19806 | 7/1995 |
| WO | WO 99/30777 | 6/1999 |
| WO | WO 2005/011475 | 2/2005 |

* cited by examiner

*Primary Examiner* — George Manuel
(74) *Attorney, Agent, or Firm* — Orrick Herrington & Sutcliffe, LLP

(57) ABSTRACT

An active implantable medical device such as a cardiac prosthesis for the treatment of a heart failure by controlled adjustment of the atrioventricular and interventricular delays. The device provides atrioventricular and/or biventricular stimulation, a sensor delivering at least one hemodynamic parameter correlated with time intervals representative of the succession of the systolic and diastolic phases, and circuits to adjust the AV delay and/or VV delay. The device determines (12) during one cardiac cycle several parameters such as the left ventricular pre-ejection interval LPEI, the left ventricular ejection time LVET, the diastolic filling time FT and the conduction time PR. The device compares (14, 18) these parameters with at least one predetermined criterion. If a condition is met, the device readjusts (16) the AV delay and/or VV delay to maximize the ventricular filling and ejection.

8 Claims, 2 Drawing Sheets

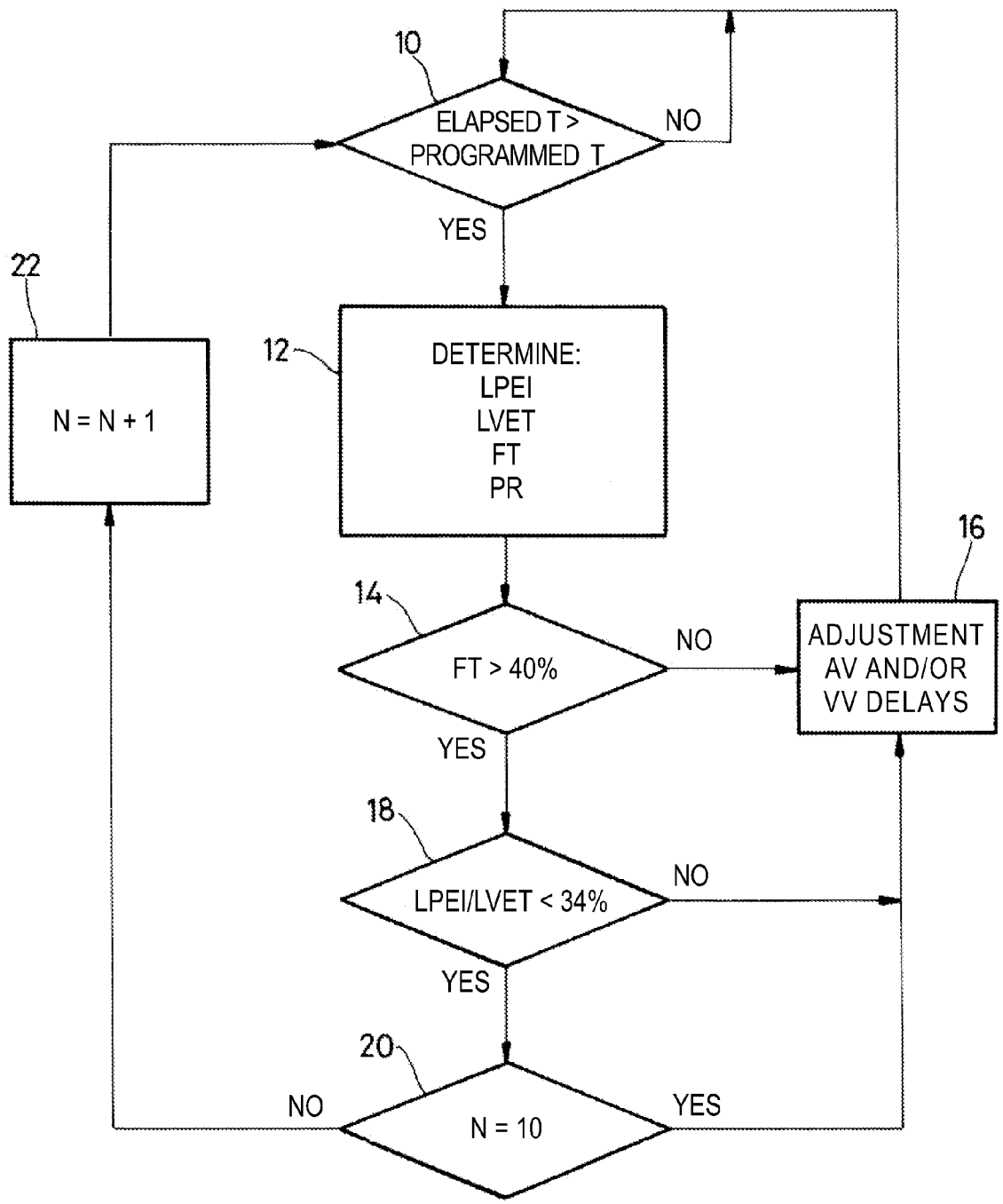
FIG_1

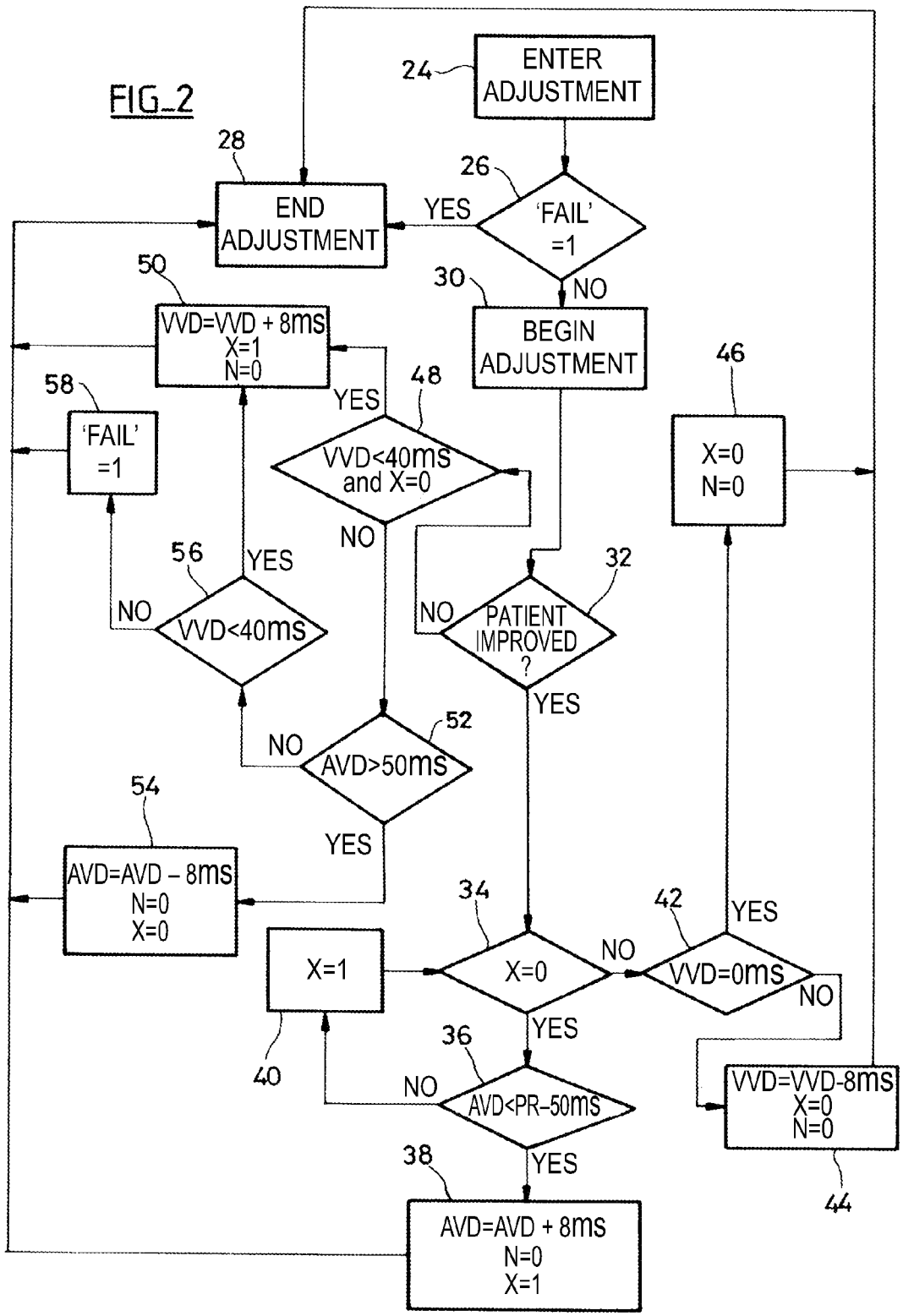

TREATMENT OF HEART FAILURE BY CONTROLLED ADJUSTMENT OF THE ATRIOVENTRICULAR AND INTERVENTRICULAR DELAYS IN AN ACTIVE IMPLANTABLE MEDICAL DEVICE

FIELD OF THE INVENTION

The present invention relates to "active implantable medical devices" as defined by the 20 Jun. 1990 Directive 90/385/EEC of the Council of the European Communities, particularly to devices that continuously monitor a patient's heart rhythm and deliver to the heart, if necessary, electrical pulses for stimulation, resynchronization, cardioversion and/or defibrillation in case a rhythm disorder is detected by the device, and more particularly to devices that provide for treatment of a heart failure, alternatively or in addition to the treatment of a cardiac rhythm disorder.

BACKGROUND OF THE INVENTION

Therapy for the treatment of a heart failure is designed to resynchronize contractions of heart chambers (atrium and ventricle, and both ventricles) in order to improve the patient's well being by optimizing different phases of a hemodynamic cycle. A hemodynamic cycle includes: pre-ejection, isovolumetric contraction, systolic ejection, isovolumetric relaxation, and finally filling of a cavity.

To optimize cardiac hemodynamics, one should:
ensure a maximum filling time between the moment the aortic valve closes and the moment the mitral valve closes, and
allow a systolic time that ensures a maximum ejection time as compared to the pre-ejection time, a condition of effectiveness of a systolic phase.

The optimization can be achieved by adjusting the atrioventricular delay and/or the interventricular delay. The atrioventricular delay, hereinafter referred to as "AV delay" (AVD), is the delay separating, during one cardiac cycle, an atrial event (e.g., an atrial contraction, either spontaneous or stimulated by the device) and the consecutive ventricular stimulation. The interventricular delay, hereinafter referred to as "VV delay" (VVD), is the delay separating, during one cardiac cycle, two ventricular stimulations respectively applied to the right and the left ventricles, said VV delay being adjusted so as to resynchronize the ventricular contractions—a technique known as CRT (Cardiac Resynchronization Therapy) or BVP (Bi-Ventricular Pacing).

EP 0 862 927 A1 and its US counterpart U.S. Pat. No. 5,995,870 (assigned to ELA Medical, now known as Sorin CRM) describes a method to adjust AVD and VVD parameters according to a ventricular contraction, detected by a sensor measuring representative variations of either the volume or either of the movement of the ventricular muscle fibers at the beginning of a systole and/or at the opening of one or both of the semilunar valves, in order to determine the moment of the opening. This detection may be operated by various types of sensors such as sensors for measuring an electrical impedance of the myocardium, contractility, and ventricular volume by magnetometry, and sensors for detecting the opening of a valve by ultrasonic transduction. These sensors may be mounted on an endocardial stimulation lead.

However, clinical experience shows that optimization of hemodynamic parameters, such as the filling time or the time of left pre-ejection are not always sufficient to achieve desired results. There is a close interrelationship between different phases of a cardiac cycle, however, the existing methods do not allow a correlation of the evolution of all cardiac phases to find optimal AVD and/or VVD parameter settings for a sufficient CRT.

The starting point of the present invention is the discovery by the inventor(s) that, for improving the hemodynamic status of a patient, optimization of hemodynamic parameters based on one of the cardiac phases is not sufficient, and a whole cardiac cycle is compromised instead of optimizing only a particular part of a cardiac cycle to the detriment of other parts of the cardiac cycle. Thus:
the optimization of the systole shall not reduce the filling time, and
the optimization of the filling time shall not reduce the effectiveness of the systole.

OBJECTS AND SUMMARY OF THE INVENTION

It is, therefore, an object of the present invention to use a combination of several hemodynamic parameters and manage their interrelationship to optimize adjustment of stimulation parameters.

Broadly, one aspect of the present invention is directed to a device of the type described in EP 0 862 927 A1 and its US counterpart U.S. Pat. No. 5,995,870 cited above, the device comprising: means for atrioventricular and/or biventricular stimulation applying during a single cardiac cycle an atrioventricular (AV) delay between atrial events and ventricular pacing, and/or an interventricular (VV) delay between ventricular stimulations in the left and right ventricles; sensor means delivering at least one hemodynamic parameter correlated with time intervals representative of the successive phases of the systolic and diastolic phases, and means for adjusting the AV delay and/or VV delay as a function of said at least one hemodynamic parameter.

According to a preferred embodiment of the present invention, the sensor means determines at least two different hemodynamic parameters during a single cardiac cycle, and the device comprises means, operating dynamically and repeatedly over several cardiac cycles, for: determining said at least two different hemodynamic parameters, checking consistency of these hemodynamic parameters with at least one predetermined criterion, and if no consistency is met, readjusting in response the AV delay and/or the VV delay.

The two hemodynamic parameters are chosen from the group consisting of: the left ventricular pre-ejection interval LPEI; the left ventricular ejection time LVET; the diastolic filling time FT; the conduction time PR and combinations of the foregoing.

According to one embodiment, the predetermined criteria include one or more of the following: the comparison of the left ventricular pre-ejection interval LPEI to a maximum threshold, the comparison of the filling time FT to a minimum threshold, the comparison of the ratio between the left ventricular pre-ejection interval LPEI and the left ventricular ejection time LVET to a maximum threshold, the comparison of the filling time FT to a minimum threshold, and/or the comparison of the ratio between the left ventricular pre-ejection interval LPEI and the left ventricular ejection time LVET to a maximum threshold.

The device preferably readjusts both the AV delay and the VV delay, within predetermined limit values of AV delay and VV delay, advantageously to adjust in priority the AV delay if it has not already reached one of the AV delay limit values, and to adjust the VV delay if the AV delay has already reached one of the AV delay limit values.

In response to the detection of an improvement in the patient's hemodynamic status from the hemodynamic parameters, it is determined to lengthen the AV delay and/or shorten the VV delay.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is a flowchart diagram explaining the basic principles of a preferred embodiment of the present invention; and FIG. 2 is a flowchart explaining how the AVD and VVD parameters are modified in the process of FIG. 1.

DETAILED DESCRIPTION OF THE INVENTION

As regards its software aspects, the present invention can be implemented by an appropriate programming of the controlling software of a known device, for example, a cardiac pacemaker or a defibrillator/cardioverter, including means for collecting a signal provided by endocardial leads and/or one or more implanted sensors.

The present invention may particularly be applied to implantable devices such as those of the Reply and Paradym device families produced and marketed by Sorin CRM, Clamart France, formerly known as ELA Medical, Montrouge, France. These devices include programmable microprocessor circuitry to receive, format, and process electrical signals collected (detected) by electrodes implanted and deliver stimulation pulses to these electrodes. It is possible to transmit by telemetry software that will be stored in a memory of the implantable devices and executed to implement the functions of the invention that will be described herein. The adaptation of these devices to implement the functions and features of the present invention is believed to be within the abilities of a person of ordinary skill in the art, and therefore will not be described in detail.

A cardiac cycle is characterized by a number of hemodynamic parameters, including:
the left ventricular pre-ejection interval LPEI (Left Pre-Ejection Interval)
the left ventricular ejection time LVET (Left Ventricular Ejection Time)
the diastolic filling time FT or DFT (Diastolic Filling Time).

Various techniques are known to determine these hemodynamic parameters, notably from the time elapsed during a cardiac cycle between the cardiac depolarization (spontaneous or stimulated) and different hemodynamic phases successively formed by: the pre-ejection the time, the isovolumetric contraction, the systolic ejection, the isovolumetric relaxation, and the filling of the cavity.

The moments of a cardiac cycle is determined by various sensors such as those mentioned in EP 0 862 927 A1 and its US counterpart U.S. Pat. No. 5,995,870 cited above, or by a technique described in EP 2 092 885 and its US counterpart US Published Application 2009/0209875, (also assigned to ELA Medical, now known as Sorin CRM), each of which is incorporated herein by reference in its entirety. The latter document, entitled "Device for an analysis of the endocardiac signal of acceleration" describes different time markers of the characteristic instants of a cardiac cycle as being determined by the analysis of an endocardial acceleration signal, a parameter measured by an accelerometer in contact with the heart muscle, preferably a sensor integrated into an endocardial lead. The data provided by such a sensor reflects precisely and in real time the contributing phenomena to the mechanical functioning of the heart, thus, after filtering and analysis of the endocardial acceleration signal, provides time markers of the systole and of other indices of the hemodynamic performance of the myocardium.

These parameters may be determined in real-time, beat by beat, to allow estimating the hemodynamic performance of the heart at each instant and to optimize the therapy to be applied, if any, to the patient.

According to one embodiment, cardiac hemodynamic parameters are optimized based on at least two criteria. For example, the criteria include:
a maximum filling time FT, ideally FT>40%. The filling time FT is the time interval between the closure of the aortic valve and the closure of the mitral valve usually expressed in relative terms, in percentage of the full length of a cardiac cycle (RR duration); and
a systolic time ensuring a maximum systolic ejection time, thus a minimum LPEI/LVET ratio, ideally LPEI/LVET<34%.

With reference to the drawings, the functionality of a device in accordance with the present invention will now be described via a process flow chart. In FIG. 1, stage 10 indicates a pre-programmed timeout, corresponding to the frequency at which the determination of hemodynamic parameters and adjustment of AV delay and/or VV is made. After the timeout period expires, the device determines (stage 12) hemodynamic parameters required for optimization, including LPEI, LVET, FT and PR.

The filling time FT is considered (test 14) to assess whether it is higher than a predetermined threshold, for example, the 40% threshold mentioned above. If this is not the case, the hemodynamic status of the patient is not satisfactory, and the device adjusts the AV and/or VV delay (stage 16, which will be explained with reference to FIG. 2 below).

If the filling time FT is lower than the predetermined threshold, the filling time FT is correct, and the device checks (test 18) whether the ejection is satisfactory, for example, by testing the LPEI/LVET ratio compared to a predetermined threshold, e.g., the 34% threshold mentioned above. If the latter criterion is not asserted, the ejection is not satisfactory and the patient's situation is improved by adjusting the AV and/or VV delay (stage 16, as above).

The process returns to the timeout stage 10, after a counter N—whose role will be clarified hereafter—is incremented (stage 22).

If the counter N reaches a certain limit, for example N=10 (test 20), the AV and/or VV delay are systematically adjusted as necessary (back to stage 16).

According to one embodiment, these settings (e.g., AV and/or VV delay) are adjusted if a slow improvement of the patient is seen as a result of a cardiac remodeling in the sense of (i) the lengthening of the AV delay while ensuring the complete capture of the left ventricle, and (ii) the reduction of the VV delay to a minimum, ideally zero (where the two ventricles contract synchronously).

FIG. 2 illustrates various stages of adjustment of AV and VV delays corresponding to the operations performed at stage 16 of FIG. 1.

The process begins at stage 24, by testing an indicator "Fail" which is a marker of a failure positioned according to the description below (stage 58) to indicate that the scaling parameter has not resulted in an improvement in the patient's condition. In such case, it is not necessary to go further (test 26), and the process ends (stage 28).

However, if the patient is not experiencing failure, the process of adjusting AV and VV delays is initiated (stage 30). If the patient's condition has improved over the past ten iterations of the process illustrated in the flowchart of FIG. 1 (test 32), the process examines an indicator X (test 34) for deciding to start the adjustment primarily by the AV delay, and then continue by the VV delay: if the indicator X is zero, the adjustment starts with the AV delay. The X indicator allows, in case of improved settings corresponding to an improved patient condition, to alternately modify the AV delay or the VV delay.

If the AV delay is too long, for example, it is shorter than the PR conduction time increased by 50 ms (test 36, AVD<PR—50 ms)), the AV delay is extended by one increment, for example, an increment of 8 ms (stage 38). At the same time, the counter N (the value that is considered at test 20 of FIG. 1) is reset, and the indicator X is set to 1 to indicate that an adjustment of the VV delay is needed, and the adjustment process is completed (back to stage 28).

If, in test 36, the AV delay is too long (AVD≧PR—50 ms), then the X flag is set to 1 (stage 40) without modifying the AV delay and resetting the counter N.

When, in stage 34, the indicator X is equal to 1, the device has already adjusted, or attempted to adjust the AV delay, and the VV delay is determined to be adjusted if necessary.

If the VV delay is at its minimum value VVD=0 (test 42), the VV delay is reduced by one increment, for example, an increment of 8 ms (stage 44). The indicator X is set to zero and counter N is reset, and the adjustment process is completed (back to stage 28).

If the test 42 indicates that the VV delay is non-zero, the VV delay has not been changed, and the device repositions the indicator X to zero, resets the counter N (stage 46), and terminates the process (back to stage 28).

Adjustments of the AV and VV delays as described above are made, if, as noted above, the device determined in stage 32 an improvement of the patient's condition.

Otherwise, the device proceeds differently, by executing stages 48 to 58. At test 48, the device determines if it is in a situation in which the VV delay is not too long (e.g., VVD<40 ms) and if the indicator X is set to zero (test 48). If the conditions at test 48 are met, the VV delay is increased by one increment, the indicator X is set to 1 and the N counter is reset (stage 50). If the conditions at test 48 are not met, the AV delay is examined to check whether it exceeds or not the minimum value that can be programmed, for example, 50 ms (test 52). If the condition at test 52 is met, the AV delay is reduced by one increment, the indicator X and the counter N are reset (stage 54).

If the condition at test 52 is not met, the device determines whether the VV delay is less than the maximum value that can be programmed (test 56). If the condition at test 56 is met, the VV delay is increased by one increment, the X flag is set to 1 and the counter N is reset (stage 50). If the condition at test 56 is not met, the failure marker "Fail" is set to 1 (stage 58), indicating that the patient's condition deteriorated despite the elongation of AV and VV delays.

If the failure condition is confirmed as marked by Fail being equal to 1, an intervention of the physician is appropriate to assess and improve the patient's condition.

One skilled in the art will appreciate that the present invention can be practiced by other than the embodiments described herein, which are presented for purposes of illustration and not of limitation.

I claim:

1. An active implantable medical device for one of cardiac stimulation, resynchronization and defibrillation, comprising:

means for applying during a single cardiac cycle at least one of an atrioventricular (AV) delay between an atrial event and a consecutive ventricular stimulation and an interventricular (VV) delay between two ventricular stimulations;

sensor means for delivering over one cardiac cycle at least two hemodynamic parameters correlated to different intervals of time representative of a succession of a systolic phase and a diastolic phase;

means for adjusting the AV delay and/or the VV delay according to said at least two hemodynamic parameters; and means, operating dynamically and repeatedly over several cardiac cycles, for:

determining said at least two hemodynamic parameters, checking for a match of said at least two hemodynamic parameters with at least one predetermined criterion, and in case of no match, readjusting in response at least one of the AV delay and the VV delay, wherein said at least one predetermined criterion is selected from among the group consisting of:

a comparison of the left ventricular pre-ejection interval LPEI to a maximum threshold;

a comparison of the diastolic filling time FT to a minimum threshold, a comparison of the ratio between a left ventricular pre-ejection interval LPEI and a left ventricular ejection time LVET to a maximum threshold, and a comparison of the filling time FT to a minimum threshold.

2. The device of claim 1, wherein the means for adjusting the AV delay and/or the VV delay adjusts the AV delay and/or the VV delay within respective predetermined limit values of the AV delay and the VV delay.

3. The device of claim 2 further comprising means for readjusting as a priority the AV delay if the AV delay has not already reached the predetermined limit value of the AV delay, and for readjusting the VV delay if the AV delay has already reached said predetermined limit value of the AV delay.

4. The device of claim 1 further comprising means for detecting an improvement of a hemodynamic status of a patient from said at least two hemodynamic parameters, and in response either lengthening the AV delay or shortening the VV delay.

5. An active implantable medical device for one of cardiac stimulation, resynchronization and defibrillation, comprising:

means for applying during a single cardiac cycle at least one of an atrioventricular (AV) delay between an atrial event and a consecutive ventricular stimulation and an interventricular (VV) delay between two ventricular stimulations;

sensor means for delivering over one cardiac cycle at least two hemodynamic parameters correlated to different intervals of time representative of a succession of a systolic phase and a diastolic phase;

means for adjusting the AV delay and/or the VV delay according to said at least two hemodynamic parameters, and means, operating dynamically and repeatedly over several cardiac cycles, for:
  determining said at least two different hemodynamic parameters,
  checking for a match of said at least two hemodynamic parameters with at least one predetermined criterion, and
  in case of no match, readjusting in response at least one of the AV delay and the VV delay,
wherein said at least one predetermined criterion is a comparison of the ratio between the left ventricular pre-ejection interval LPEI and the left ventricular ejection time LVET to a maximum threshold.

6. The device of claim 5, wherein the means for adjusting the AV delay and/or the VV delay adjusts the AV delay and/or the VV delay within respective predetermined limit values of the AV delay and the VV delay.

7. The device of claim 6 further comprising means for readjusting as a priority the AV delay if the AV delay has not already reached the predetermined limit value of the AV delay, and for readjusting the VV delay if the AV delay has already reached said predetermined limit value of AV delay.

8. The device of claim 5 further comprising means for detecting an improvement of a hemodynamic status of a patient from said at least two hemodynamic parameters, and in response either lengthening the AV delay or shortening the VV delay.

* * * * *